US012012377B2

(12) United States Patent
Zellhuber et al.

(10) Patent No.: US 12,012,377 B2
(45) Date of Patent: Jun. 18, 2024

(54) METHOD AND SYSTEM FOR PRODUCING ONE OR MORE OLEFINS AND ONE OR MORE CARBOXYLIC ACIDS

(71) Applicant: LINDE GmbH, Pullach (DE)

(72) Inventors: Mathieu Zellhuber, Martinsried (DE); Martin Schubert, Munich (DE); Andreas Meiswinkel, Rimsting (DE); Florian Winkler, Munich (DE); Desislava Tota, Munich (DE); Hans-Jörg Zander, Munich (DE)

(73) Assignee: LINDE GmbH, Pullach (DE)

( * ) Notice: Subject to any disclaimer, the term of this patent is extended or adjusted under 35 U.S.C. 154(b) by 689 days.

(21) Appl. No.: 15/734,497

(22) PCT Filed: Jun. 19, 2019

(86) PCT No.: PCT/EP2019/066308
§ 371 (c)(1),
(2) Date: Dec. 2, 2020

(87) PCT Pub. No.: WO2019/243480
PCT Pub. Date: Dec. 26, 2019

(65) Prior Publication Data
US 2021/0230093 A1    Jul. 29, 2021

(51) Int. Cl.
*C07C 5/48* (2006.01)
*B01J 8/04* (2006.01)
(Continued)

(52) U.S. Cl.
CPC .............. *C07C 5/48* (2013.01); *B01J 8/0496* (2013.01); *C07C 11/04* (2013.01); *C07C 51/215* (2013.01);
(Continued)

(58) Field of Classification Search
CPC ....... C07C 51/215; C07C 11/04; C07C 53/08; C07C 5/48; B01J 8/0496; B01J 2208/00044
See application file for complete search history.

(56) References Cited

U.S. PATENT DOCUMENTS

2010/0256432 A1    10/2010    Arnold et al.

FOREIGN PATENT DOCUMENTS

| CN | 1636632 A   | 7/2005 |
|----|-------------|--------|
| CN | 103958453 A | 7/2014 |

(Continued)

OTHER PUBLICATIONS

Tang, et al., Preparation of acetic acid by direct oxidation or ethane, Petrochemical Technology, vol. 4, No. 32, pp. 337-342 (Year: 2003).*

(Continued)

*Primary Examiner* — Yate' K Cutliff
(74) *Attorney, Agent, or Firm* — COZEN O'CONNOR

(57) ABSTRACT

The invention relates to a method for producing one or more olefins and one or more carboxylic acids, in which one or more paraffins is or are subjected to an oxidative dehydrogenation. For the oxidative dehydrogenation, a reactor (10) having a plurality of reaction zones (11, 12, 13) is used, a gas mixture comprising the one or more paraffins is successively passed through the reaction zones (11, 12, 13), and at least two of the reaction zones (11, 12, 13) are subject to varying temperature influences. The invention also relates to a corresponding system (100).

14 Claims, 6 Drawing Sheets

(51) Int. Cl.
*C07C 11/04* (2006.01)
*C07C 51/215* (2006.01)
*C07C 53/08* (2006.01)

(52) U.S. Cl.
CPC ..... *C07C 53/08* (2013.01); *B01J 2208/00044* (2013.01)

(56) References Cited

FOREIGN PATENT DOCUMENTS

| EP | 0261264 | * | 9/1986 | ............... C07C 5/48 |
| EP | 0261264 | A1 | 3/1988 | |
| RU | 2214383 | C1 | 10/2003 | |
| RU | 2335485 | C2 | 10/2008 | |
| RU | 2344116 | C1 | 1/2009 | |
| RU | 2612305 | C1 | 3/2017 | |
| WO | WO 2014090714 | A1 | 6/2014 | |
| WO | WO-2017144584 | A1 * | 8/2017 | ............... B01J 8/04 |
| WO | WO 2017144584 | A1 | 8/2017 | |
| WO | WO 2018019761 | A1 | 2/2018 | |

OTHER PUBLICATIONS

Chinese Patent Application No. CN201980040749.X, Office Action dated Feb. 24, 2023, with English translation, 20 pages.
Tang, H. et al., "Preparation of acetic acid by direct oxidation of ethane" Petrochemical Technology 2003, No. 32. vol. 4, pp. 337-342.
Russian Patent Application No. 202013875204, Office Action dated Dec. 19, 2022, with English translation, 18 pages.
Russian Patent Application No. 202013875204, Search Report dated Dec. 16, 2022, with English translation, 7 pages.
PCT/EP2019/066308 International Search Report and Written Opinion dated Aug. 7, 2019; 7 pages.

* cited by examiner

METHOD AND SYSTEM FOR PRODUCING ONE OR MORE OLEFINS AND ONE OR MORE CARBOXYLIC ACIDS

The invention relates to a method for producing one or more olefins and one or more carboxylic acids and to a corresponding system according to the preambles of the independent claims.

PRIOR ART

Oxidative dehydrogenation (ODH) of paraffins having two to four carbon atoms is generally known. In the case of ODH, said paraffins are reacted with oxygen to give, inter alia, the respective olefins and water.

The ODH may be advantageous over more established processes for preparing olefins such as steam cracking or catalytic dehydrogenation. There is no thermodynamic equilibrium limitation due to the exothermicity of the reactions involved and the virtually irreversible formation of water. The ODH can be carried out at comparatively low reaction temperatures. In principle, no regeneration of the catalysts used is required, since the presence of oxygen enables regeneration in situ. Ultimately, in contrast to steam cracking, lower amounts of valueless by-products such as coke are formed.

For further details regarding the ODH, reference is made to the relevant technical literature, for example Ivars, F. and Lopez Nieto, J. M., Light Alkanes Oxidation: Targets Reached and Current Challenges, in: Duprez, D. and Cavani, F. (eds.), Handbook of Advanced Methods and Processes in Oxidation Catalysis: From Laboratory to Industry, London 2014: Imperial College Press, pages 767-834, or Gärtner, C. A. et al., Oxidative Dehydrogenation of Ethane: Common Principles and Mechanistic Aspects, ChemCatChem, Vol. 5, No. 11, 2013, pages 3196 to 3217.

WO 2017/144584 A1 discloses a reactor for the ODH in which two reaction zones are present. Two separate coolant circuits are used and different catalysts are present in the reaction zones.

In the case of ODH, particularly when MoVNbTeOx catalysts are used under industrially relevant reaction conditions, significant amounts of the respective carboxylic acids of the paraffins used are formed as by-products. In this connection, reference is likewise made to relevant technical literature such as Li, X. and Iglesia E., Kinetics and Mechanism of Ethane Oxidation to Acetic Acid on Catalysts Based on Mo—V—Nb Oxides, J. Phys. Chem. C, Vol. 112, 2008, pages 15001 to 15008. For economic system operation, a corresponding coupling production of olefins and of the respective carboxylic acids using the catalyst type described is generally unavoidable. This applies in particular to the preparation of ethylene by ODH of ethane (ODH-E) in which acetic acid is formed at the same time, but also for further cases explained in more detail below.

In industrial practice, coupling production methods are generally considered to be less attractive, since they always involve limited production flexibility. In order to make such a method attractive, an easily controllable, flexible system must be made available to the operator in order to allow the simplest possible adaptation of the product distribution to the actual and/or economically reasonable demand. In certain cases, it may be desirable in corresponding processes to shift the product distribution in the direction of one of the products formed, for example in the direction of ethylene in the case of ODH-E, particularly if there is better marketability (larger market volume) for the respective product.

Furthermore, the highest possible selectivity to the desired product and a maximum conversion of the reagents are desirable in order to reduce investment and operating costs as a result of the smaller gas volumes to be processed. The present invention addresses this object.

DISCLOSURE OF THE INVENTION

Against this background, the present invention proposes a method for the production of one or more olefins and one or more carboxylic acids and a corresponding system with the features of the independent patent claims. Embodiments are the subject matter of the dependent claims and the following description.

Streams of material, gas mixtures, etc. may be rich or low in one or more components in the language used herein, wherein the term "rich" may represent a content of at least 95%, 96%, 97%, 98%, 99%, 99.5%, 99.9% or 99.99% and the term "low" may represent a content of at most 5%, 4%, 3%, 2%, 1%, 0.5%, 0.1% or 0.01% on a molar, weight, or volume basis. When a plurality of components is specified, the specification "rich" or "low" refers to the sum of all components. If, for example, reference is made to "oxygen" or "ethane", this may be a pure gas, but also a mixture rich in the respective component.

In the following, the terms "pressure level" and "temperature level" are used to characterize pressures and temperatures, which means that pressures and temperatures do not have to be used in the form of precise pressure or temperature values. For example, a pressure level or temperature level may be ±1%, 5%, 10%, 20% or 50% above or below an average. A plurality of pressure and temperature levels may represent disjointed or overlapping regions. The same pressure or temperature level can also be present, for example, when pressures and temperatures have reduced due to line losses or cooling. The pressure levels indicated in bar here are absolute pressures.

Advantages of the Invention

As mentioned, for economic system operation, the coupled production of ethylene and acetic acid when using the described catalyst type in the ODH, particularly the ODH-E, is generally inevitable, although in industrial practice, coupling production methods are generally considered to be less attractive. The embodiment of a flexible, catalytic process is challenging, especially if it is an exothermic process such as ODH, in particular ODH-E. In this case, the risk of a thermal passage must always be prevented, which in part severely restricts the adjustment of the operating parameters. Furthermore, the catalytic processes include a plurality of partial reactions which mutually influence one another. As a rule, it is therefore very difficult to identify suitable process variables which reliably describe the reaction and which are suitable as a process control. The same applies to the reactor design and to the design of the catalyst or catalysts used.

If, in the following, reference is made in simplified terms to the production of ethylene and acetic acid, this does not exclude the possibility that higher olefins and carboxylic acids can also be formed within the context of the method according to the invention, in particular when using corresponding feeds which also contain higher paraffins in addition to ethane. While during steam cracking, for example, lighter olefins can also be formed from heavier paraffins, for example from propane ethylene, this is not necessarily the case with ODH, in particular ODH-E. For example, propane is predominantly converted here to propylene and acrylic acid (propenoic acid), but not to ethylene. However, a further reaction may also occur to give lighter products, for example by converting acrylic acid by elimination of carbon dioxide to give ethylene, which then reacts further to form acetic acid. A corresponding reaction is described, for example, in Naumann d'Alnoncourt, L.-I. et al., Journal of Catalysis, Vol. 311, pp. 369 to 385. If the subject here is "the production of an olefin and a carboxylic acid", the olefin and the carboxylic acid may have the same or different number of carbon atoms, even though they are formed from only one reactant. The present invention also explicitly does not exclude the possibility that a plurality of different olefins and/or carboxylic acids can be formed from one or more different reactants.

The carboxylic acids formed in the ODH are typically separated with water from a process gas flow formed in the ODH. If paraffins of different chain lengths are used, an aqueous solution of different carboxylic acids is obtained. If this, and the simultaneous formation of higher olefins, is not desired, a reaction feed can also be formed in such a way that it does not contain any higher paraffins, for example by means of a separation provided upstream. The present invention is particularly suitable for use in connection with ODH-E, but also for the production of higher olefins and carboxylic acids through the ODH of corresponding longer-chain (heavier, higher), in particular linear, paraffins.

In conventional reactors of real-life size, a practical limitation of the ethane conversion, for example at 40 to 45%, can be determined in ODH-E. A further increase in the conversion leads to rapidly increasing losses in by-products such as carbon oxides (COx) and thus also to an increased risk of thermal throughput. At the same time, it was found that the product ratio of ethylene to acetic acid in ODH-E depends on the water partial pressure in a process gas at the reactor outlet. The water partial pressure in turn depends to a significant degree on the water content in the reaction feed and on the reaction conversion. A desired increase in the ethane conversion would lead to higher water partial pressure at the reactor outlet and thus inevitably to a shift in the product distribution in the direction of acetic acid. In addition, it has been found that, for continuous operation of a reactor for the ODH-E, it is necessary to maintain a minimum water dilution in the reaction feed, since otherwise a significant time decrease in activity and thus catalyst performance occurs.

The present invention is based on the insight that the problems described above can be solved at least in part by using a reactor having a plurality of reaction zones. Within the plurality of reaction zones, within the context of the present invention, a temperature influence is effected to different extents, specifically in such a way that a minimum reaction temperature is maintained overall in the reactor or it is ensured that the reaction temperature does not drop below a predetermined value in the direction of the reactor outlet. This is achieved by selectively influencing the temperature, i.e. influencing the temperature to different extents, in the individual reaction zones. "Influencing the temperature to different extents" in the plurality of reaction zones is understood in the context of the present invention to mean that in at least one of the reaction zones, a temperature is influenced in a manner which deviates from a temperature influence in at least one of the other reaction zones.

In principle, "temperature influencing" in the context of the present invention can comprise heating or cooling of a corresponding reaction zone. A degree of heating can be set in particular by adjusting the catalyst loading and/or catalyst activity per space unit in a corresponding reaction zone. Since with higher catalyst loading and/or catalyst activity per space unit, the heat released in each case is correspondingly increased (i.e. the temperature is influenced to a greater extent), the reaction temperature can be correspondingly increased through higher catalyst loading and/or catalyst activity per space unit. However, the reaction temperature can also be increased by virtue of the fact that in a reaction zone in which a higher reaction temperature is to be obtained, a lesser degree of cooling or a higher degree of heating is carried out by means of a corresponding temperature control agent. The present invention may encompass both alternatives individually or in a useful combination with each other.

In particular, the present invention may be used with multi-layer catalyst beds, which are each provided in one or more reaction tubes of a respective reactor. In contrast to the use of a single-layer catalyst bed or a reactor with only one reaction zone, the present invention opens up further opportunities for an economical optimization of corresponding processes. However, the simple use of a multilayer catalyst bed or a reactor with corresponding reaction zones is not necessarily sufficient for this purpose, since without the use of further measures, a shift of the product distribution to acetic acid could occur due to the higher water partial pressure.

A reactor used in the context of the present invention can in particular be designed as a tubular reactor, i.e. as a reactor which has a plurality of reaction tubes running at least partially parallel. Here, each of the reaction tubes passes through the corresponding reaction zones or is formed with corresponding reaction zones. Here, a multilayer catalyst bed can be formed in each of the reaction tubes and/or each of the plurality of reaction tubes can be subjected to different temperature control along its length to different extents by means of a temperature control unit, so that temperature-influenced reaction zones are formed along the reaction tubes to different extents. If a "tubular reactor" is referred to below, this can in particular be a known tube bundle reactor. The terms mentioned are used synonymously in this case. Reference is made to common textbooks with regard to the construction and operation of tube bundle reactors.

In the context of the present invention, despite increased conversion rates, a shift in the value product selectivity to more ethylene can be achieved overall compared to the operation of a reactor with only one corresponding reaction zone. This is achieved at the same vapor dilution rates in the reaction feed. The advantages of the present invention result from the fact that in the direction of the reactor outlet, the reaction temperature can be raised above a value which is higher than the value which would result with continuous or constant reactor design. The reaction temperature must be limited at the reactor inlet in the conventional manner so that a maximum reaction temperature is not exceeded. However, as has been recognized according to the invention, a corresponding restriction proves to be not advantageous in the subsequent reaction zones, since at the reactor outlet it leads to the minimum advantageous reaction temperature being undershot. However, a deviating temperature control proposed according to the invention ensures that this minimum reaction temperature is not undershot.

A particular advantage of the present invention is that in the provision of catalyst beds or corresponding reaction zones which have different catalyst loadings and/or catalyst activities per space unit, only layers with variable catalyst activity have to be used, i.e. only the proportion of inert material in the catalyst particles can be changed, but the formulation of the active catalyst material itself can be kept the same for all catalyst beds or reaction zones. In this way, in the context of the present invention, the advantageous production of large amounts of catalyst is possible, which is only "diluted" to varying extents with inert material in corresponding catalyst beds or reaction zones. Using corresponding measures, a particularly simple way of influencing temperature to different extents can be achieved in the respective reaction zones.

Overall, against this background, the present invention proposes a method for preparing one or more olefins and one or more carboxylic acids. As already explained, the present invention relates in particular to the ODH-E, i.e. to a case in which a corresponding olefin is ethylene and a corresponding carboxylic acid is acetic acid. In other words, in this case, the number of carbon atoms is two in each case, and an olefin and a carboxylic acid are formed. However, as mentioned, the method can also be used for the production of higher olefins, for example for the production of propylene and propenoic acid from propane, the number of carbon atoms being three. In the context of the present invention, however, the number of carbon atoms may also be four or optionally five. However, the focus of the present invention is ODH-E and the invention will be described below in particular with reference to ODH-E.

In the method according to the invention, one or more paraffins is or are subjected to oxidative dehydrogenation. The principles of oxidative dehydrogenation have already been explained in the introduction. In the context of the present invention, the oxidative dehydrogenation is carried out, as mentioned, in particular in a tubular reactor which in particular has a number of reaction tubes through which the corresponding gas mixture flows longitudinally. The reaction tubes are passed in particular through a jacket space through which a temperature control agent flows. In one embodiment of the present invention, the jacket space can also be divided, so that the reaction tubes can be differently temperature-controlled in sections. Here, sections of the reaction tubes each form one reaction zone. Each of the reaction tubes contains a support structure for holding a catalyst material (i.e. the active catalyst and inert diluent components, also referred to as a "catalyst bed").

A "catalyst bed" refers here in particular to a bed which is introduced into a corresponding reactor or a reaction tube of a corresponding reactor at a specific position and which comprises inert material and active catalyst. Corresponding regions of different reaction tubes can be equipped with catalyst beds of identical properties, in particular in sections. This can also be understood to mean that in this case, a catalyst bed is distributed to different reaction tubes. The dilution of the active catalyst material with inert material is preferably conducted during the production of corresponding bulk bodies which form a catalyst bed, and can be carried out in such a way that different bulk bodies with different proportions of active catalyst material are provided. In this case, a catalyst bed with a predetermined activity level consists entirely of identical bulk bodies with the corresponding proportion of active catalyst material. In another embodiment, different reaction zones with reduced catalytic activity can also be provided by physical mixing of inert bulk bodies and bulk bodies with a higher proportion of active catalyst material.

In the context of the present invention, a reactor having a plurality of reaction zones is used for the oxidative dehydrogenation, wherein a gas mixture with the one or more paraffins is passed successively through the reaction zones, and wherein at least two of the plurality of reaction zones have a catalyst of the same type of catalyst and/or are subjected to a temperature influence to different extents. As mentioned, in general, two approaches can be implemented in order to influence the temperature in this manner.

If it is meant here that two reaction zones have a catalyst "of the same catalyst type", it should be understood that identical catalysts are present in the reaction zones with regard to their composition or formulation in the same or (by corresponding dilution with inert material) different concentration. In particular, the corresponding zones each have one or two identical MoVNbTeOx catalysts which catalyze the ODH.

In particular, a reactor can be used for the oxidative dehydrogenation, in which the plurality of reaction zones is formed as a layered structure from a plurality of catalyst beds or as reaction zones separated from one another with one catalyst bed each. A formation of corresponding reaction zones in the form of multilayer catalyst beds, which in this case form a plurality of catalyst beds, is also generally possible within the context of the present invention. Here, a gas mixture containing the aforementioned paraffin is passed successively through said reaction zones. In this embodiment of the present invention, the catalyst bed of a second of said reaction zones, through which the gas mixture is passed after it has previously been passed through a first one of the reaction zones, is formed with a higher catalyst loading and/or catalyst activity per space unit than the catalyst bed of the first reaction zone.

The proposed solution according to the invention has in particular the advantage that compared with only one reaction zone, both the conversion of the paraffin used and the selectivity to the corresponding olefin can be significantly increased by a plurality of reaction zones and thus an ODH-E process can be operated in a markedly more economical way.

In a pilot reactor used by the Applicant, when it was operated with one only single-zone bed, maximum ethane conversions were achieved, which could not be further augmented in the single-zone case, since this would have entailed a thermal runaway of the reactor. In the case of a multi-layer catalyst bed, at otherwise identical conditions with regard to the space velocity, pressure and composition of the reaction feed, further increased ethane conversions were achieved without having the risk of thermal throughput.

The solution according to the invention comprises that this also effectively results in different (reaction) temperatures in the different zones, wherein the different reaction temperatures can be achieved, for example, by an increase in the catalyst activity in the direction of flow and/or a zonally varying cooling/temperature control of the reactor.

In other words, in this embodiment the present invention provides an increase in catalyst loading and/or catalyst activity in the direction of the reactor outlet and by contrast, a reduction in the direction of the reactor inlet. The catalyst loading and/or catalyst activity can here be adjusted in particular by means of different degrees of dilution by means of inert material, wherein the active catalyst material can in particular be identical in the different reaction zones. In the context of the present invention, the catalyst loading and/or catalyst activity is increased stepwise, in particular from zone to zone, which, in contrast to a gradual increase, enables a particularly simple provision of the respective catalyst bed by admixing a respectively fixed amount of inert material or using the same bulk bodies. Corresponding measures can be combined with a further stepped temperature control of the reaction zones.

The use of a multilayer catalyst bed or of a reactor with corresponding reaction zones thus proposed in the context of the embodiment of the present invention just explained can achieve an increase in the conversion of ethane or another paraffin with only small losses of total value products (defined here as the sum of the olefin or olefins, and of the carboxylic acid or carboxylic acids, in particular of ethylene and acetic acid). Within the context of the present invention, in particular a maximum temperature is maintained or, through the choice of the catalyst activity or catalyst loading, it is ensured that a corresponding maximum temperature is not exceeded. Corresponding advantages can also be achieved by means of a different temperature control using suitable temperature control units, or with a combination of corresponding measures.

In the context of a corresponding embodiment of the present invention, as explained below, the catalyst loading or catalytic activity per space unit that increases in the direction of flow or a graduated temperature control can be used to prevent excess formation of carboxylic acid production in such regions by maintaining a minimum temperature which results from the respectively present catalyst loading and/or catalyst activity, or the respectively adjusted exothermicity and/or the respectively performed tempering.

A basic feature of the present invention is that the determination of the individual catalyst loadings or catalyst activities, as well as the dimensioning of the reaction zones or their catalyst beds, or a corresponding stepped temperature control, are each carried out in such a way that a process gas temperature is not undershot in an inadmissible way in any of the catalyst beds.

In a particularly advantageous aspect of the present invention, a minimum and a maximum reaction temperature are therefore predetermined and the influencing of the temperature, i.e. the catalyst loading and/or the catalyst activity per space unit and/or a corresponding temperature control in the catalyst beds, is conducted in such a way that the maximum reaction temperature is not exceeded in any of the reaction zones at any respective given position, and the minimum reaction temperature is not undershot.

As mentioned, such a formation of the catalyst beds or the reaction zones may also comprise a corresponding dimensioning of the catalyst beds or reaction zones. In particular, in the context of the present invention, in the direction of the reactor outlet, where the highest partial pressures of the olefin or olefins and the lowest partial pressures of the paraffin or paraffins are achieved, a correspondingly increased catalyst loading and/or catalyst activity is implemented or provided, whereby it can be ensured that here, the minimum predetermined reaction temperature is not undershot. Since in the direction of the reactor outlet, the partial pressures of the paraffin or paraffins are significantly lower than at the start, a higher catalyst activity is advantageously also provided, so that the "remaining" paraffins can still be converted in sufficient quantity (and thus also that the required heat for the minimum temperature can be generated).

In the context of the present invention, as mentioned several times, a reactor is advantageously used which uses a number of reaction tubes running at least partially in parallel. This is therefore a crude reactor of the generally known type or a tube bundle reactor. In particular, it is provided that the predetermined position at which the maximum reaction temperature is not to be exceeded and the minimum reaction temperature is not to be undershot lies on a central axis of at least one of the plurality of reaction tubes.

However, it may also be provided within the context of the present invention to permit to a certain extent an exceeding and undershooting of corresponding temperature limits. For example, it can be provided that the method is carried out in such a way that the maximum reaction temperature is not exceeded and the minimum reaction temperature is not undershot in at least 30%, 60%, 80%, 90%, 95% or 99% of each of the reaction zones. Here, in particular, increased minimum requirements in the direction of the reactor outlet can also be defined. In other words, a corresponding method can be carried out in such a way that the minimum reaction temperature is not undershot in the second reaction zone at a higher percentage of the catalyst bed than in the catalyst bed of the first reaction zone.

The advantages of the present invention result in particular from the fact that irrespective of possible intermediate desorption and adsorption steps after the formation of ethylene or the olefin, the formation of acetic acid from ethylene (or other carboxylic acids starting from corresponding olefins) has a significantly lower activation energy and thus a significantly lower temperature dependence than the other main reactions during the ODH. This applies in particular in comparison with the formation of ethylene or a corresponding other olefin starting from ethane, or of the corresponding paraffin, but also in comparison with the various reactions which lead to the formation of carbon oxides, i.e. undesired by-products.

In the context of the present invention, the activation energies were quantified on the basis of laboratory experiments with different feed compositions. This observation of the catalyst behavior is particularly noteworthy, since at elevated temperatures, the formation of all higher oxidized products, such as acetic acid, carbon monoxide and carbon dioxide, should be facilitated. However, when studying reactions in ODH-E reactors operating under industrial conditions, it could be shown by the Applicant that the formation reactions of carbon monoxide and carbon dioxide from higher temperatures are disproportionately facilitated over the formation reaction of acetic acid. In principle, the reaction rates of all reactions, i.e. here, the formation rates of all products, increase with an elevation in temperature. However, the distinct difference in the activation energies, in particular the significantly lower activation energy of the subsequent reaction ethylene to acetic acid (and thus the significantly lower temperature dependence of this reaction) compared with all other reactions, causes the further reaction of the ethylene or the formation rate of acetic acid to be increased to a lesser extent by the further reaction of the ethylene relative to the other reactions (main reactions, ancillary reactions and subsequent reactions). This causes the observed selectivity shift. However, it should be emphasized that the mechanism described need not necessarily be based on the experimentally observed effects, and the invention is therefore not limited by the explanations just given.

From fundamental considerations and without this surprising finding according to the invention, the person skilled in the art would not have considered it necessary to maintain a certain minimum temperature in a reaction zone or in a catalyst bed, since they would have assumed that with an increase in temperature, increasing amounts of acetic acid would be formed to an equal degree. However, as could be shown in the context of the present invention, the opposite is the case. It is surprising that precisely acetic acid, which is not desirable in the context of the present invention, is formed in a comparatively enhanced manner at lower temperatures. A person skilled in the art would have assumed that the formation of acetic acid at an elevated temperature would be enhanced in a similar manner, and therefore would not have selected or operated a reactor having an embodiment as suggested by the present invention. They would therefore have remained with a correspondingly simpler mode of operation or reactor design.

The present invention utilizes the highly different temperature dependencies of the individual reactions during ODH in order to control not only the conversion and the overall selectivity to value products, but also the selectivity distribution between these value products, through targeted influencing of the temperature conditions.

In the context of the present invention, a tubular reactor is used in particular, which is designed such that it has an inlet opening and an outlet opening, wherein at least two of the mentioned reaction zones are provided and arranged between the inlet opening and the outlet opening of the reactor. Here, one of the reaction zones, which is arranged closer to the outlet opening than another of the reaction zones, is equipped with an increased catalyst loading and/or catalyst activity per space unit, or is cooled to a lesser extent than the other of the reaction zones. In other words, in the context of the present invention, on the reactor outlet side, increased catalyst loading and/or catalyst activity is selected per space unit, or a lower cooling is carried out. In the context of the invention, the increased catalyst activity or a lower cooling can in particular also be carried out only in the "last" reaction zone or in a corresponding catalyst bed, and the previously arranged catalyst beds or corresponding reaction zones can have lower, in particular gradually lower, catalyst activities and/or catalyst loadings per space unit, or can be correspondingly cooled more strongly. As mentioned, the catalyst activities can intensify stepwise from zone to zone in the direction of the reactor outlet. The same applies in the case of a tempering performed within the context of the invention.

In particular, it can be provided that the reactor has at least one further reaction zone, through which the gas mixture is passed before it is passed through the first reaction zone and the second reaction zone. In this case, provision is made in particular for the second reaction zone to be formed with a higher catalyst loading and/or catalyst activity per space unit than the catalyst bed of the first reaction zone, or to carry out a further reduced cooling. As mentioned, the further reaction zone may also have a lower catalyst loading and/or lower catalyst activity per space unit than the first reaction zone or its catalyst bed.

The catalysts which can be used in the context of the present invention have already been mentioned above. In particular, the same catalysts or catalysts having the same basic formulation can be used in all catalyst beds or reaction zones in the context of the present invention. These can be provided in different concentrations or contents per space unit, wherein a dilution can be carried out as mentioned above. In particular, all reaction zones or their catalyst beds can each have a portion of the active catalyst of at least 0.1% by weight. The active catalyst content may also, for example, be greater than 1, greater than 5, or greater than 10% by weight of the active catalyst share. The respective content depends on the activity of the catalyst. If a different temperature control of the individual reaction zones is carried out, the catalyst may optionally also be kept completely the same over the entire length of the reaction tubes. Any combination is possible.

In the context of the present invention, it is provided in particular that the reaction zones are tempered by means of a temperature control system using one or more temperature control agent flows. In particular, a temperature control system with different temperature control agent flows, which selectively temperature-control specific reaction zones or catalyst beds, can be used. In this way, a particularly targeted adaptation to the respectively required maximum and minimum temperatures can be achieved. Thus, in particular, at least one of the temperature control agent flows can be used for the temperature control of only one or only a part of the reaction zones. A "tempering" takes place in particular in the form of cooling. This can be carried out in particular by means of liquid salt. Here, an increasingly lesser degree of cooling can be carried out in particular in the direction of the reactor outlet.

The present invention is also based on the surprising finding that at a water partial pressure at the outlet of one or more reactors used for the ODH-E in the range of 0.5 to 5 bar (abs.), in particular of 0.7 to 3 bar (abs.), the molar flow ratio of acetic acid to ethylene in the outlet flow (hereinafter predominantly referred to as "process gas") is almost linear to the water partial pressure at the outlet. This value can therefore be used as a process control if a specific product ratio of acetic acid to ethylene is to be set. The water partial pressure in the process gas is the result both of the addition of water at the reactor inlet or in a corresponding reaction feed and of the conversion of the ethane in the reactor and thus possibly also of the current catalyst activity. In contrast to setting only the water content in the reaction feed, which without knowledge of said further influencing factors can lead to highly fluctuating water partial pressures in the process gas, and thus to varying product ratios, a much more precise adjustment of the desired product ratio can therefore be achieved by using the water partial pressure in the process gas as a process control. At the same time, in the context of the present invention, by using a minimum amount of water in the reaction feed, a constant catalyst activity can be maintained, which otherwise would decrease over time.

An adjustment of the water content in the reaction feed, but not in the process gas, is described in EP 1 201 630 A2. Furthermore, it is also stated here that the pressure, temperature and dwell time in the reaction zone can be controlled. However, the level of the water content in the process gas is not addressed here. The same also applies to a method described in U.S. Pat. No. 4,899,003 A. In both cases, it is thus missing from the finding that the water partial pressure at the reactor outlet represents a process control, via which the product selectivity of a method in which coupling production of ethylene and acetic acid by means of ODH-E is carried out using the aforementioned type of catalyst can be set particularly reliably.

The cited regularities were initially found in the context of ethane oxidation test series with a constant inlet temperature and varying water proportion in the reaction feed using a MoVNbTeOx catalyst. In this case, an almost constant conversion of the ethane could be achieved, with likewise virtually constant selectivity to carbon dioxide and carbon monoxide. In contrast, the molar amounts of the desired products ethylene and acetic acid developed contrary to one another in precisely this range. The stated range shows a continuous, almost linear, opposite course of the product molar flow ratio of acetic acid to ethylene. For further explanation, reference is made to the attached FIGS. 2 and 3 and the associated explanations.

In addition, analogous series of experiments were carried out at different flow rates and thus at different space velocities (Weight Hourly Space Velocity, WHSV) and temperatures in the reactor. As expected, at a higher flow rate and thus at a higher space velocity and lower temperature, lower conversion rates are observed, but at equal water partial pressures at the reactor outlet, the ratio of the two product molar flows is virtually identical to the values determined at a lower flow rate. This shows that the process control in the aforementioned region can be based to a considerable degree on the water partial pressure at the outlet. The partially clear linear course of the product molar flow ratio becomes apparent above all for the economically relevant operation at higher conversions.

Further series of experiments were carried out using a test reactor, wherein the above-mentioned relationships could also be demonstrated. For details, reference is made in particular to the attached FIG. 6 and the associated explanations.

The present invention therefore proposes, in a particularly advantageous embodiment, that a water-containing process gas be removed from the reactor and that a water partial pressure be set in the process gas, in particular depending on a predetermined product ratio, in particular a predetermined product molar flow ratio, from the acetic acid to the ethylene or another carboxylic acid to the corresponding olefin, to a value in a range of between 0.5 and 5 bar (abs.), in particular in a range of between 0.7 and 3 bar (abs.). As mentioned, a consistently continuous, almost linear product molar flow ratio of acetic acid to ethylene or the other compounds mentioned results in the range for different conversions and operating conditions, so that a particularly well controllable coupling production of these compounds with an adjustable production center is possible here.

In the context of the present invention, a shift in the value product selectivity to more ethylene can be achieved overall despite increased conversion rates compared with operation with a single-layer catalyst bed or a reactor having only one corresponding reaction zone. This is achieved at the same vapor dilution rates in the reaction feed. The described measures for controlling the development of catalyst activity over time by adjusting different water partial pressures in the gas mixture removed from the reactor remain valid even when a multilayer bed is used, and are advantageous in particular when combined.

The characteristic selectivity curves can thus be shifted parallel towards more ethylene when an adequately designed, multilayer catalyst bed or a reactor having a plurality of corresponding reaction zones is used. The adaptation possibilities during operation on the basis of the control of the water partial pressure at the reactor outlet is thus maintained. The same also applies to the case of a zonally different temperature control.

The limitations in the further economic optimization of the process described when using a single-layer bed can thus be overcome by using a process control with multilayer beds and targeted temperature control. The economic viability and the marketability of ODH and ODH-E technology are thus noticeably improved.

In the context of the present invention, the oxidative dehydrogenation is subjected to a gas mixture which, in addition to the paraffin or paraffins, also comprises oxygen and in particular diluents. This gas mixture can, in particular, also be fed to the reactor or reactors used in the form of separate streams of material and thus be formed only in the reactor or reactors. For example, a paraffin-containing material flow and an oxygen-containing material flow may be combined to form a corresponding reaction feed in the reactor or reactors used or upstream of the reactor or reactors.

The gas mixture or one or more components thereof can undergo any process treatment such as compression, expansion, cooling or heating or also the separation of partial flows, the addition of further material flows or a chemical reaction of components. In particular, in the context of the present invention, the formation of a corresponding gas mixture comprises for example heating. During this heating, the so-called feed preheating, the gas mixture can be brought to a temperature which allows the ODH to start up in a reaction unit which is connected to one or more reactors.

In particular, in one method according to one embodiment of the invention, it may be provided that the formation of the gas mixture comprises combining a flow of material with one or more further fluids. In this way, suitable media can be fed which, for example, favorably influence the reaction conditions in the case of ODH. As mentioned, the ODH is a highly exothermic reaction so that typically, so-called diluents such as inert gases or steam, are added to prevent thermal runaway. Corresponding diluents can be added during the formation of the gas mixture, i.e. upstream or only in one or more reactors. Oxygen or an oxygen-containing gas mixture which is required in the case of ODH can also be added, for example, already during the formation of the gas mixture. Optionally, this also takes place only later.

In the context of the present invention, the water partial pressure is advantageously measured and a control is used by means of which the water partial pressure is adjusted using at least one control variable. As mentioned, a control based on the water partial pressure can achieve a much more precise adjustment of the product ratio than if only a water addition in the reaction feed were to be controlled.

As mentioned, the present invention is used in particular when a catalyst containing at least the elements molybdenum, vanadium, niobium and optionally tellurium, that is to say a so-called MoVTeNbO catalyst, is used in the oxidative dehydrogenation, because ethylene and acetic acid form when such a catalyst is used and the aforementioned regularities occur.

In the context of the present invention, the oxidative dehydrogenation is advantageously carried out with a paraffin conversion of at least 15%. The ethane conversion can in particular be at least 20, 25, 30, 35, 40, or 45%. The paraffin conversion is in particular below 75%. The predetermined product molar flow ratio of acetic acid to ethylene or another carboxylic acid to another olefin is in particular in a range from 0.05 to 0.5.

The term "conversion" here means the molar proportion of the reactants used, here the ethane or another paraffin, which reacts overall to (main and ancillary) products. The "product molar flow" of a component describes the molar amount of a component which exits one or more reactors per unit of time.

In the context of the present invention, the water partial pressure in the process gas can be adjusted in particular by adding water to the reaction feed flow and/or by adjusting a reactor temperature at which the oxidative dehydrogenation is carried out. In this connection, the zonally different temperature influencing, as proposed by the present invention, can be used in particular. These are therefore suitable control variables for the aforementioned control. It can also be provided, for example, to conduct a rough adjustment by adding water to the gas mixture supplied to the reactor and a fine adjustment by adjusting a reactor temperature. At a higher reactor temperature, a higher conversion results and thus a higher formation of reaction water. Here, the water partial pressure in the process gas is thus at least partially adjusted by adjusting the reactor temperature.

The added amount of oxygen in the reaction feed is a further decisive influencing variable. In the context of the present invention, in the particularly advantageous refinement, this parameter is always adapted such that at the reactor outlet, an oxygen content in the process gas between 0.01 mol % and 50 mol %, preferably between 0.1 and 5 mol %, particularly preferably between 0.1 and 0.5 mol %, is always maintained in order firstly to avoid a reduction of the catalyst material due to lack of oxygen and secondly to limit safety risks due to high oxygen contents. However, these restrictions result in the fact that the regulation of the oxygen addition is downstream of the fundamental determination of the operating point and has no appreciable influence on the product molar flow ratio, as long as it is ensured that the aforementioned range for the oxygen content at the outlet is maintained.

In the context of the present invention, the water partial pressure to be adjusted is understood to mean the partial pressure at a reactor outlet of one or more reactors used for oxidative dehydrogenation, for example directly at the end of a catalyst bed or a line connected thereto. In particular, a process gas from the oxidative dehydrogenation at the reactor outlet has not yet been subjected to measures that change its composition, in particular cooling, washing, or the like.

It is particularly advantageous when the water partial pressure at the reactor outlet of the reactor or reactors is identified and used as the input variable of a regulation. Methods for determining the water and thus for determining the water partial pressure are generally known to the person skilled in the art. For example, these may be common absorption spectroscopy methods, such as Fourier-transformed infrared spectroscopy (FTIR) or tunable diode laser absorption spectroscopy (TDLAS), in combination with common pressure measurement methods.

In the context of the present invention, the oxidative dehydrogenation is particularly advantageously carried out in a temperature range or at a temperature level of 240 to 500° C. in a reactor bed of the reactor or reactors used. In particular, the temperature range may be at 260 and 400° C., particularly preferably at 280 to 350° C. The total pressure at the reactor inlet of the reactor or reactors is preferably between 1 and 10 bar (abs.), in particular between 2 and 9 bar (abs.), more particularly between 3 and 8 bar (abs.). The space velocity in the reactor bed of the reactor or reactors (WHSV) is in the range between 0.1 and 10 kg of paraffin/(h×kg of catalyst), preferably between 0.5 and 5 kg of paraffin/(h×kg of catalyst), particularly preferably between 0.7 and 3 kg of paraffin/(h×kg of catalyst). The previously explained adjustability of the product molten flows is possible in this region in particular.

The method according to the invention can in particular be carried out using one or more diluents added to the reaction feed and transferred into the process gas. The use of suitable diluents, which in particular ensure that stable and reliable reactor operation is ensured in the case of highly exothermic ODH, is known in principle. As mentioned, in particular an addition of water or water vapor into the reaction feed can take place in order to set the desired water partial pressure in said region. This water or this water vapor simultaneously acts as a diluent. Alternatively, or additionally, however, one or more further diluents may be used.

In particular, one or more diluents selected from the group consisting of water, methane, nitrogen and at least one further inert gas may be employed within the context of the present invention. Carbon dioxide can also be used as diluent. Corresponding diluents do not participate in the reaction in the reactor or reactors, or at best to a small extent, and therefore pass at least predominantly into the process gas.

In the context of the present invention, it has furthermore been recognized that, in the case of ODH-E, even when ethylene is introduced as an additional feed flow into the reactor, i.e. as part of the reaction feed, there is a strong functional relationship between the product molar flow ratio of ethylene and acetic acid and the water partial pressure at the reactor outlet. The described system operation can thus also be applied with additional ethylene supply. This makes it possible, for example, to increase the flexibility towards more acetic acid as product, if this is desired. However, this leads to expected higher losses to carbon monoxide and carbon dioxide. Thus, in certain cases, a method variant may be advantageous in which ethylene is further added to the reaction feed in a predetermined amount, in particular from 0 to 50 mole percent. The same applies to other olefins.

The introduction of additional ethylene can take place both in the form of a supply from an external source and in the form of a return of a corresponding fraction from the decomposition part of the system itself. The "decomposition part" is an arrangement in which components or component groups are separated from the process gas or a gas mixture obtained therefrom by means of thermal separation. This recycling can be effected by additional removal of a corresponding fraction in the decomposition part or by changing the bottom product specification in a rectification column which is used for separating ethane and ethylene, and which is provided in the decomposition part. In this case, by adapting the separation conditions such as top temperature or pressure, or else by using a correspondingly formed, "less precisely" separating rectification column, a portion of the product ethylene, which is otherwise removed over the top, is transferred specifically into the bottom of the rectification column and is stripped off there in an otherwise predominantly ethane-containing fraction. This can be recycled into the reactor or reactors.

The present invention further extends to a system for producing one or more olefins and one or more carboxylic acids. For further features and advantages of a corresponding system, reference is expressly made to the corresponding independent patent claim and the above explanations. In particular, such a system is designed to carry out a method in accordance with the specific embodiments explained above and has suitable means for this purpose. Reference is also made in this respect to the above explanations.

In order to achieve a particularly advantageous embodiment, the system comprises means which are designed to remove a process gas containing water from the reactor and to set a water partial pressure in the process gas removed from the reactor to a value in a range between 0.5 and 5 bar (abs.), in particular in a range of between 0.7 and 3 bar (abs.), in particular depending on a predetermined product ratio of acetic acid to ethylene or another carboxylic acid.

The invention will be explained in greater detail below with reference to the accompanying drawings, which among other things illustrate preferred embodiments of the present invention.

BRIEF DESCRIPTIONS OF THE DRAWINGS

DETAILED DESCRIPTION OF THE DRAWINGS

In the following figures, elements functionally or structurally corresponding to one another are indicated by identical reference symbols and are not explained repeatedly for the sake of clarity. If system parts are described below, the explanations relating to these also apply analogously to the method steps implemented by means of these system parts and vice versa.

Figure 1:
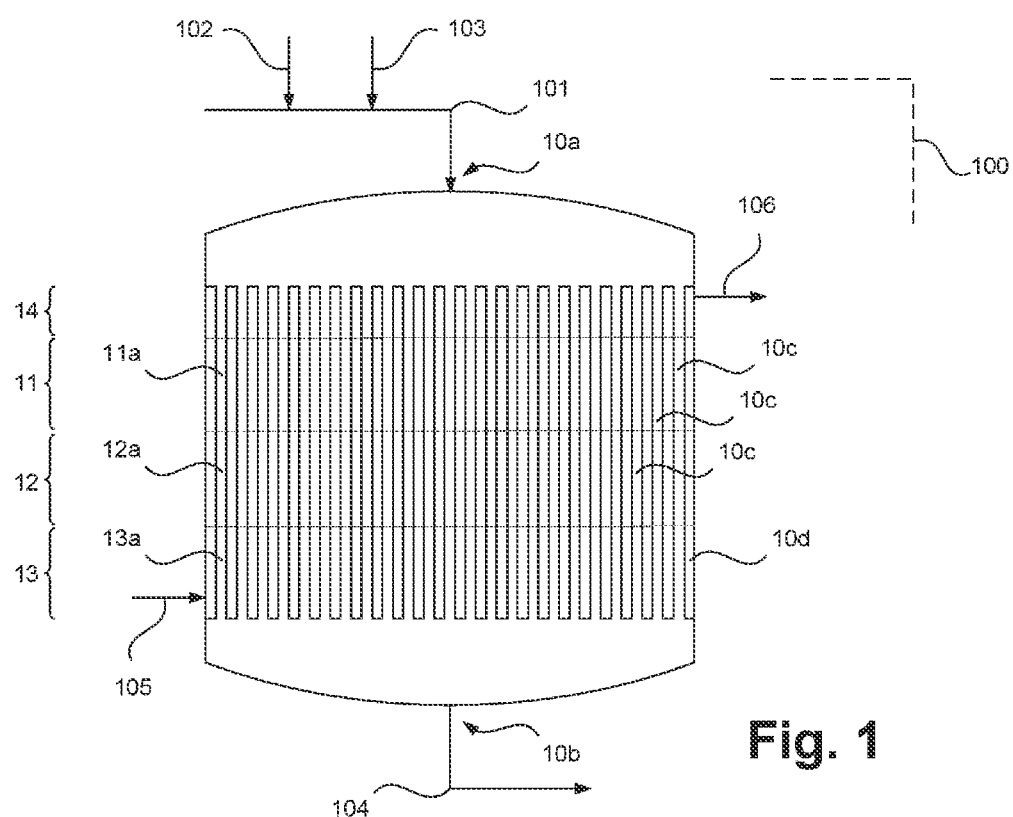
FIG. 1 illustrates a system for producing ethylene and acetic acid with a reactor according to an embodiment of the invention.

FIG. 1 illustrates a system for producing olefins in accordance with an embodiment of the invention in the form of a highly simplified system diagram and is designated generally by 100. The system 100 is only indicated schematically here. Although a system 100 for the ODH of ethane (ODH-E) is described below, as mentioned, the present invention is also suitable for use in the ODH of higher hydrocarbons. In this case, the following explanations apply accordingly.

The system 100 has a reactor 10 to which, in the example shown, an ethane-containing gas mixture obtained in any way required is fed in the form of a material flow 101. The material flow 101 can be taken, for example, from a rectification unit not shown, which separates higher hydrocarbons from an initial mixture. The material flow 101 may also be preheated and otherwise prepared, for example. The material flow 101 may already contain oxygen and optionally a diluent such as water vapor, but corresponding media may also be added to the reactor upstream or in the reactor 10 as representatively illustrated herein in the form of material flows 102 and 103.

The reactor 10 has a plurality of reaction tubes 10c arranged in parallel (marked only in part), which run through a plurality of reaction zones 11, 12, 13 which are three in number in the example shown, and which are surrounded by a jacket region 10d. In the reaction tubes 10c, a catalyst bed 11a, 12a, 13a is provided in each case in the corresponding reaction zones (only illustrated on one reaction tube 10c). A gas mixture containing ethane and oxygen and optionally a diluent is passed in succession through the reaction zones 11, 12, 13 in the form of the material flow 101 or the combined material streams 101 to 103. An inert zone 14 is connected upstream of the reaction zones 11, 12, 13. The reaction zones 11, 12 13 are arranged between an inlet opening 10a and an outlet opening 10b of the reactor 10, wherein one of the reaction zones, here the reaction zone 13, which is arranged closer to the outlet opening 10b than another of the reaction zones, here one of the reaction zones 11 and 12, is referred to as a "second" reaction zone and one of the other reaction zones 11, 12 is referred to as a "first" reaction zone. The catalyst bed 13a of the second reaction zone 13, through which the gas mixture is passed after it has previously been passed through the first reaction zone 11, 12, is in particular formed with a higher catalyst loading and/or catalyst activity per space unit than the catalyst bed 11a, 12a of the first reaction zone 11, 12. This leads to the advantages which are also explained again with reference to FIGS. 7 and 8. Alternatively or additionally, a zonally different temperature control can also take place.

A process gas flows out of the reactor 10 in the form of a process gas flow 104 containing ethylene formed in the reactor 10 through the ODH of a portion of the ethane in the reaction feed flow. Further, the process gas contains acetic acid that has also been formed from ethane during the ODH in the reactor 10, water, carbon monoxide, carbon dioxide, unconverted oxygen, as well as the diluent or diluents and other compounds, if these have been added or have previously formed in the reactor 10. The reaction tubes 10c are temperature controlled by means of a temperature control agent flow 105, 106 which is passed through the jacket region. As not illustrated here, in particular a plurality of temperature control medium circuits can be provided which temperature control or cool the reaction tubes 10c in sections.

It goes without saying that the system 100 can have one, but also a plurality of reactors 10, which are operated in parallel, for example, as illustrated. In the latter case, corresponding reaction feeds, which may be of identical or different composition, are respectively supplied to these reactors 10 and corresponding process gas flows 104 are formed in each case. The latter can, for example, be combined and supplied together as process gas to subsequent method steps or system parts.

A water partial pressure can be identified downstream of the reactor 10. This can be adjusted, for example, by adding water or steam to the gas mixture of the material flow 101 or in the form of the material flows 102 or 103. Further influencing, in particular fine adjustment, can be effected by adjusting the temperature in the reactor 100.

Subsequent method steps or system components are not illustrated. The process gas can be brought into contact therein with washing water or a suitable aqueous solution, as a result of which the process gas can in particular be cooled and acetic acid can be washed out of the process gas. The process gas, which is at least largely freed of acetic acid, can be further processed and subjected to separation of ethylene. Ethane contained in the process gas may be recycled into the reactor 10.

Figure 2:
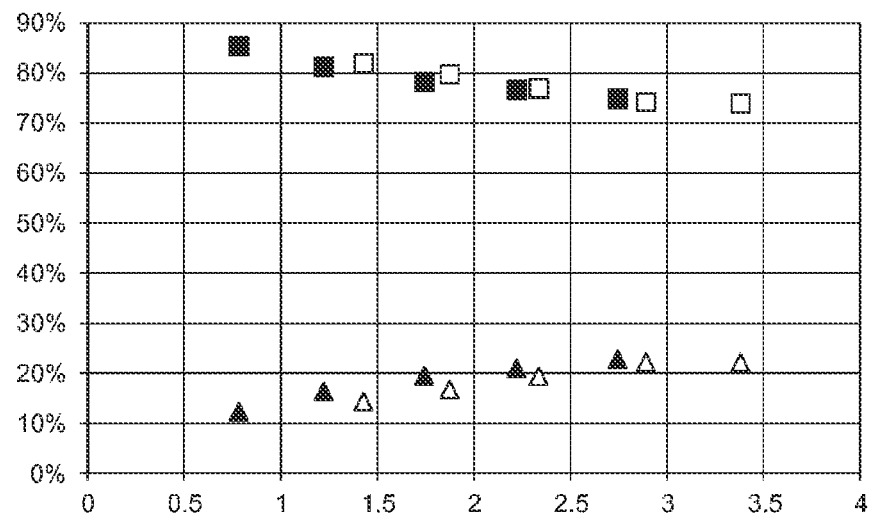
FIG. 2 illustrates selectivities to ethylene and acetic acid.

FIG. 2 illustrates selectivities to ethylene and acetic acid obtained in a corresponding process in a diagram, in which water partial pressures in bar (abs.) in a process gas flowing out of a reactor are plotted on the abscissa against selectivity values shown as a percentage on the ordinate. The selectivity values shown for the individual products are calculated from the ratio of the respective product molar flow relative to the molar amount of ethane, which is converted per unit of time in the reactor.

The data shown relate to two series of tests with different flow rates, thus to different space velocities and different temperatures. In both series of experiments, no ethylene was added at the reactor inlet. As expected, at higher flow rates, lower conversions occur (approx. 19% as opposed to approximately 40%), but the product selectivities and thus the product molar flow ratio (corresponding here to the ratio of the two selectivities) are virtually identical at the same water partial pressures at the reactor outlet. This shows that the process control in the aforementioned region can be based to a considerable degree on the water partial pressure at the outlet.

The values obtained at the higher flow rates and lower conversion rates are illustrated for ethylene with filled (black) squares and for acetic acid with filled (black) triangles, while the values obtained at the lower flow rates and higher conversion rates are correspondingly illustrated for ethylene with unfilled (white) squares and for acetic acid with unfilled (white) triangles.

Figure 3:
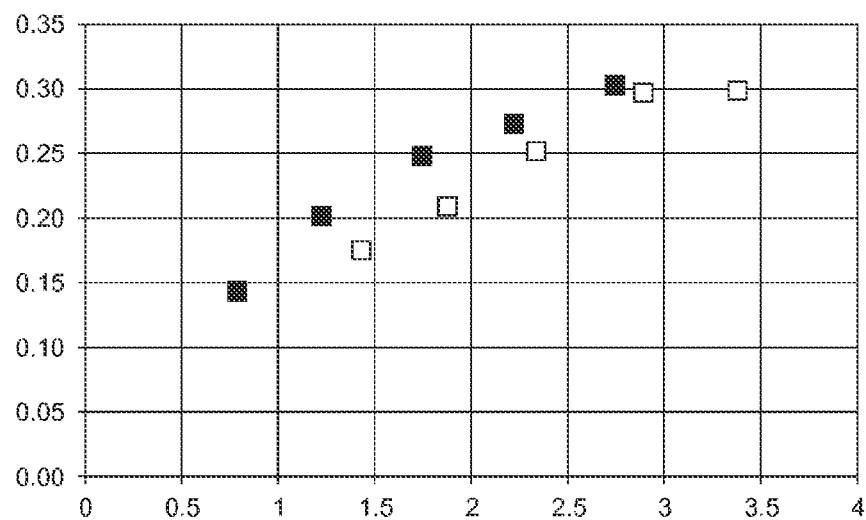
FIG. 3 shows product molar flow ratios in relation to ethylene and acetic acid to illustrate the background of the invention.

The ratio of the product quantities as a function of the water partial pressure at the reactor outlet is again illustrated in FIG. 3. Here, the water partial pressures in bar (abs.) on the abscissa are plotted against the product molar flow ratio of acetic acid to ethylene (corresponding here to the ratio of the values shown in FIG. 2 to each other). Here, the product molar flow ratios for the higher flow rates and lower conversion rates are illustrated with filled (black) squares and for the lower flow rates and higher conversion rates with unfilled (white) squares. The partially clearly linear course of the product mix is evident above all for the economically relevant operation at higher conversions.

This simplified behavior of the reaction system can be explained by two effects, which could be proven experimentally, but which are explicitly indicated here as being non-binding: On the one hand, the oxidation of ethylene formed is facilitated at elevated water partial pressures, wherein the selectivity for the formation of acetic acid increases. At the same time, desorption of the acetic acid formed from the catalyst surface is facilitated by increased water partial pressures, as a result of which less acetic acid of the subsequent oxidation of acetic acid to carbon monoxide and carbon dioxide likewise occurring on the catalyst is available. This results in the shift of the overall selectivity toward acetic acid, with virtually constant selectivity to carbon monoxide and carbon dioxide.

Figure 4:
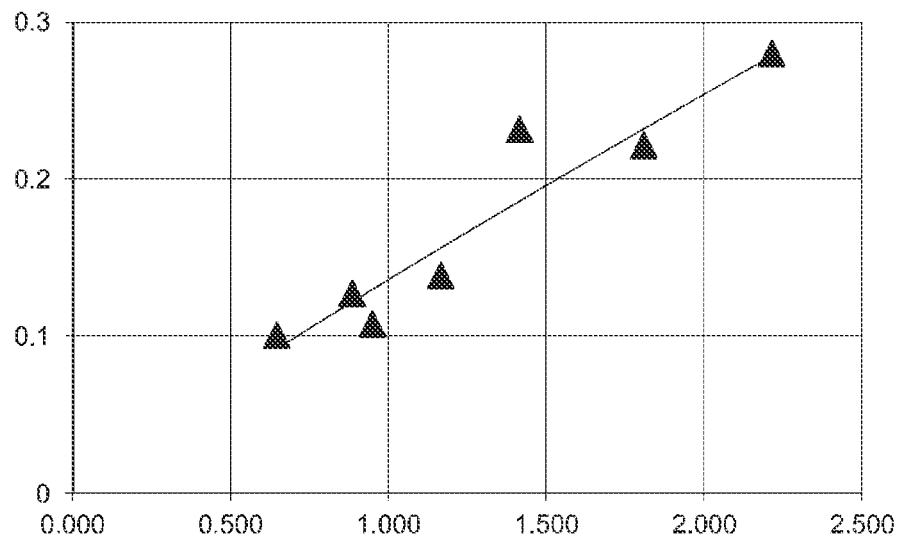
FIG. 4 shows product molar flow ratios in relation to ethylene and acetic acid to illustrate the background of the invention.

The determining influence of the water partial pressure at the outlet on the product ratio between acetic acid and ethylene can be demonstrated by further measurements, partly using different dilution media and widely varying experimental conditions. Reference is made to FIG. 4, which shows corresponding product molar flow ratios of acetic acid to ethylene. The illustration corresponds to that of FIG. 3.

Figure 5:
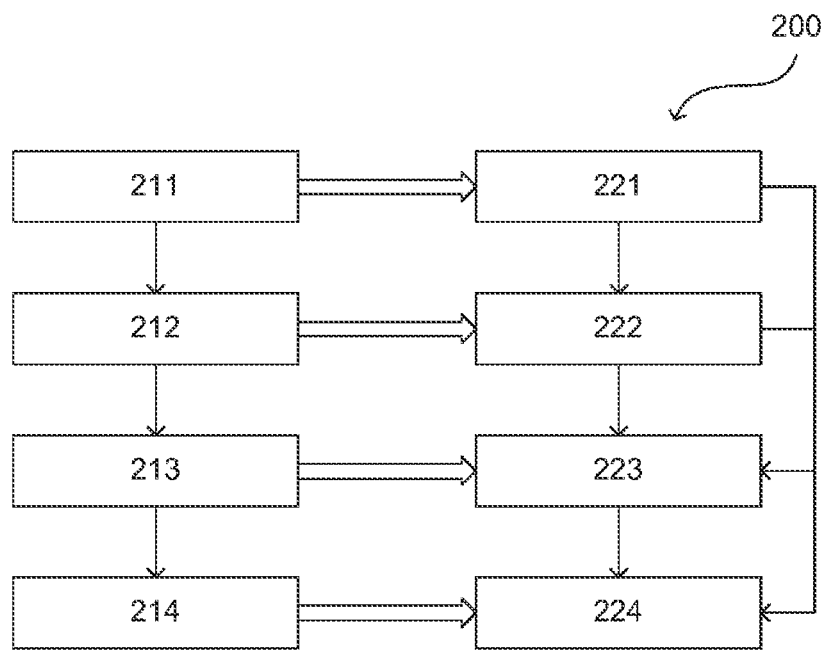
FIG. 5 illustrates a method that can be used in the context of an embodiment of the present invention.

FIG. 5 illustrates a corresponding method in the form of a schematic flow diagram, generally designated 200. In each case, 211 to 214 denotes partial objectives to be achieved, with 221 to 224 denoting the settings or specifications specifically to be implemented for this purpose.

The desired product distribution of acetic acid to ethylene is given in step 211. Based on this, a target value for the water partial pressure at the reactor outlet is established in step 221. On the basis of a total product quantity predetermined in step 212 and associated recycling quantities, a flow rate and thus the conversion in the reactor (see in particular FIGS. 2 and 3) is established in step 222.

In step 213, a correspondingly defined operating point is approached, for which purpose a water content in the reaction feed flow is adjusted in step 223. The fine tuning of the operating point, step 214, is performed by adjusting the reactor temperature in step 224. The water partial pressure at the reactor outlet is observed in each case.

Figure 6:
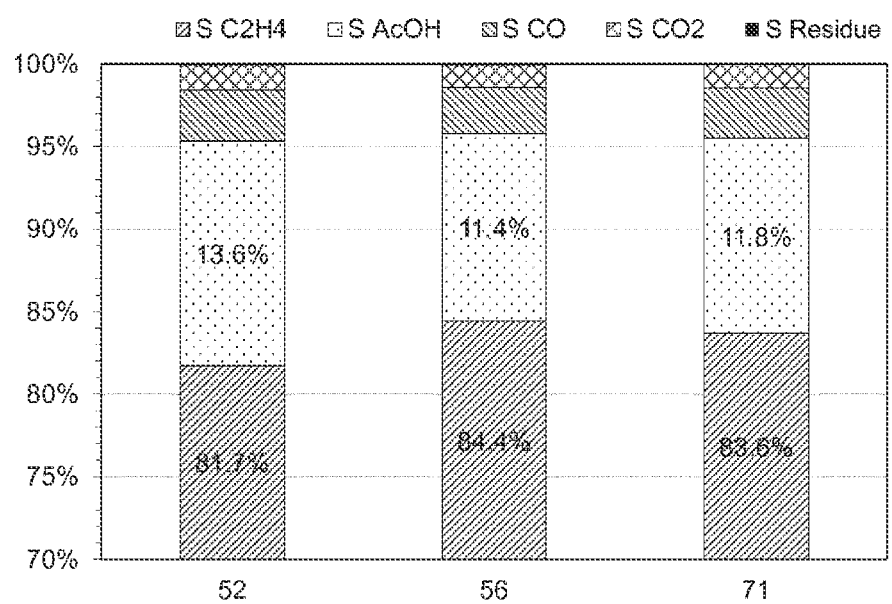
FIG. 6 illustrates product selectivities within the context of a non-inventive method.

FIG. 6 illustrates the results of three selected experiments 52, 56 and 71 performed within the context of an extensive series of experiments using a pilot reactor. In turn, a strong correlation of the product ratio of ethylene to acetic acid to the water partial pressure at the outlet of the reactor was observed within the context of the entire experimental series. This applies to different conversions and different process conditions, i.e. changed compositions, current quantities, pressures and temperatures.

Experiments 52 and 71 were carried out at the same space velocities of 0.9 kg of ethane/(kg of catalyst×h); in experiment 56, on the other hand, this was 1.4 kg of ethane/(kg of catalyst×h). The water partial pressures at the reactor inlet were 0.56 bar for experiment 52, 0.58 bar for experiment 56 and 0.46 bar for experiment 71. In other words, in experiments 52 and 56, nearly identical water partial pressures were used at the reactor inlet and, in experiment 71, the water partial pressure at the reactor inlet clearly decreased. The water partial pressures at the reactor outlet were 1.28 bar for experiment 52, 0.99 bar for experiment 56 and 1.00 bar for experiment 71. In other words, almost identical water partial pressures were therefore observed at the reactor outlet in experiments 56 and 71, and in experiment 52, the water partial pressure at the reactor outlet deviated significantly. The different water partial pressures at the reactor outlet between experiments 52 and 56 resulted from the different space velocities at substantially equal water partial pressures at the reactor inlet.

The experimental conditions for experiments 52, 56 and 71 are summarized again in the table below. The salt temperature here represents the temperature of a molten salt which was used for cooling the reactor and therefore forms a reference for the reactor temperature:

| Experiment no. | 52 | 56 | 71 |
| --- | --- | --- | --- |
| Reactor inlet pressure [bar (abs.)] | 3.81 | 3.67 | 3.10 |
| Space velocity [kg of ethane/(kg of catalyst × h)] | 0.9 | 1.4 | 0.9 |
| Water/ethane [mol/mol] | | 0.26 | |
| Oxygen/ethane [mol/mol] | 0.35 | 0.31 | 0.33 |
| Salt temperature [° C.] | 302 | 316 | 311 |
| Water partial pressure reactor inlet [bar (abs.)] | 0.56 | 0.58 | 0.46 |
| Water partial pressure reactor outlet [bar (abs.)] | 1.28 | 0.99 | 1.00 |

In experiment 52, a feed with 56.7 mole percent ethane, 19.6 mole percent oxygen, 14.8 mole percent water and 8.9 mole percent nitrogen, in experiment 56, a feed with 60.2 mole percent ethane, 18.4 mole percent oxygen, 15.8 mole percent water and 5.7 mole percent nitrogen, and in experiment 71, a feed with 57.3 mole percent ethane, 18.8 mole percent oxygen, 14.9 mole percent water and 9.0 mole percent nitrogen were used.

FIG. 6 illustrates values for selectivity (S) for ethylene (C2H4), acetic acid (AcOH), carbon monoxide (CO), carbon dioxide (CO2) and residual compounds (residue not visible due to low values) for the three experiments 52, 56 and 71. Here, the ordinate shows the values with regard to the selectivities. The ethane conversion varied by no more than 5% in the three experiments 52, 56 and 71

It can clearly be seen that in experiments 56 and 71, similar product ratios are observed at similar water partial pressures at the outlet, with different water partial pressures at the inlet. The product molar flow ratio of acetic acid to ethylene (corresponding here to the ratio of the corresponding selectivities) is in each case around 0.14 in experiments 56 and 71. In experiments 52 and 56, on the other hand, similar water partial pressures are present, but due to the changed space velocities, significantly different water partial pressures are present at the outlet. Despite similar water partial pressures at the inlet, clearly different product ratios also result for the test points 52 and 56. The product molar flow ratio of acetic acid to ethylene is around 0.17 for experiment 52 and is thus far higher than the above-mentioned value for experiment 56.

In the context of the present invention, a shift in the value product selectivity to more ethylene can be achieved overall despite increased conversion rates compared to the operation of a single-layer catalyst bed or a reactor having only one corresponding reaction zone. This is achieved at the same vapor dilution rates in the reaction feed. Provisions for controlling the development of the catalyst activity over time by adjusting a water partial pressure in the reaction feed or the gas mixture flowing out of a corresponding reactor retain their validity even when a multilayer bed is used.

The characteristic selectivity curves shown can thus be shifted parallel to more ethylene when an adequately designed, multilayer catalyst bed or a reactor having a plurality of corresponding reaction zones is used. The adaptation possibilities during operation on the basis of the control of the water partial pressure at the reactor outlet is thus maintained.

The limitations in the further economic optimization of the process described when using a single-layer bed can thus be overcome by using a process control with multilayer beds and targeted temperature control. The economic viability and the marketability of the ODH-E technology are thus noticeably improved.

Figure 7:
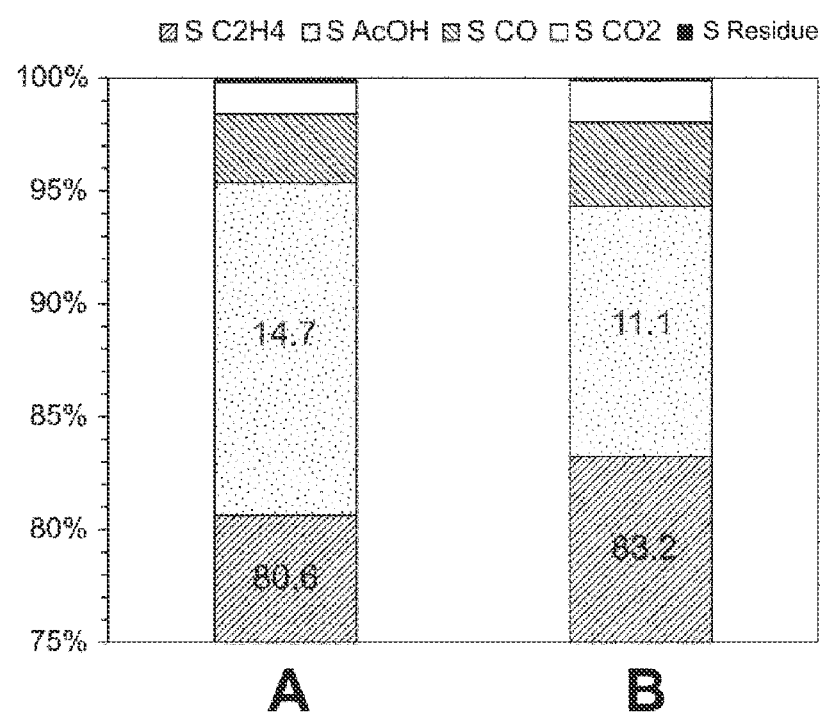
FIG. 7 illustrates product selectivities within the context of a non-inventive method and within the context of a method according to an embodiment of the invention.

FIG. 7 shows, comparable to FIG. 6, values for selectivity (S) for ethylene (C2H4), acetic acid (AcOH), carbon monoxide (CO), carbon dioxide (CO2) and residual compounds (residue, not visible due to low values), although for case A of a conventional single-layer catalyst bed reactor, and for case B of a multilayer catalyst bed, in this case for a three reaction zone reactor, having increasing catalyst activities or catalyst contents per space unit. The ordinate here also shows the values with regard to the selectivities. Identical compositions of the reaction feed and identical mass streams were used in each case.

In both cases A and B, no appreciable increase in the conversion could be achieved by a further increase in temperature without an increased risk of a thermal throughput or a significantly increased formation of carbon oxides occurring. When using a three-layer bed or three corresponding reaction zones, however, a minimum temperature higher by 15 K can be set in the respective catalyst zones, as a result of which, in case B, a significant increase in conversion and ethylene selectivity can be achieved compared to case A. The associated value product losses toward carbon oxides are low.

In 100% of all three reaction zones or their catalyst beds, process temperatures on the central axis of at least 318.5° C. were maintained. In 100% of the last two reaction zones in the direction of the reactor outlet (case B), even process temperatures on the central axis of at least 327° C. are maintained. In comparison, the minimum temperature in the entire single-layer bed (case A) is 303.5° C., and is 310° C. at the end of the catalyst bed.

Figure 8:
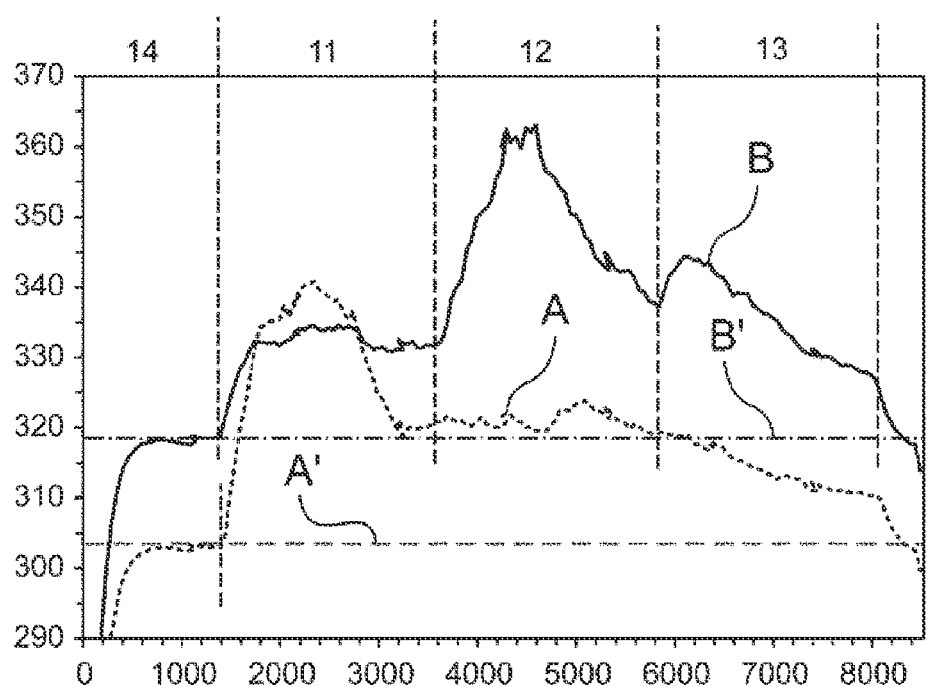
FIG. 8 illustrates reactor temperature curves within the context of a non-inventive method and within the context of a method according to an embodiment of the invention.

In FIG. 8, corresponding temperature curves are again illustrated by a reactor 10 for the cases also denoted here by A and B, wherein a reactor length in mm is indicated on the abscissa and a temperature is shown in ° C. on the ordinate. The reaction zones, also designated 11, 12 and 13 here, are present only in case B. In case A, instead of the three reaction zones designated 11, 12 and 13, only one reaction zone is present. In both cases, an inert zone 14 is present upstream of the reaction zone or reaction zones. Also illustrated are coolant (liquid salt) temperatures denoted A' and B'.

The invention claimed is:

1. Method for producing ethylene and acetic acid, in which ethane is subjected to an oxidative dehydrogenation, wherein a reactor (10) having a plurality of reaction zones (11, 12, 13) is used for the oxidative dehydrogenation wherein a gas mixture comprising the ethane is successively passed through the reaction zones (11, 12, 13), wherein at least two of the plurality of reaction zones (11, 12, 13) comprise catalysts of a same catalyst type and are subjected to varying temperature influences, wherein the catalysts of the same catalyst type are catalysts comprising molybdenum, vanadium, and niobium in the same basic formulation which are provided in different concentrations or contents per unit space, and wherein the oxidative dehydrogenation is performed in a temperature range of 240 to 500° C. and a pressure range at an inlet of the reactor of 1 to 10 bar absolute pressure.

2. Method according to claim 1, wherein in a second of the reaction zones (13) through which the gas mixture is passed after it has previously been passed through a first reaction zone (11, 12), it is formed with a higher catalyst loading and/or with a higher catalyst activity per space unit than the first reaction zone (11, 12).

3. Method according to claim 1, wherein a minimum and a maximum reaction temperature are predetermined and in which the temperature is influenced in the reaction zones (11, 12, 13) in such a way that the maximum reaction temperature is not exceeded in any of the reaction zones (11, 12, 13) at any given position and the minimum reaction temperature is not undershot.

4. Method according to claim 3, wherein a reactor (10) is used which comprises a number of at least partially parallel reaction tubes (10c), wherein the predetermined position lies on a central axis of at least one of the plurality of reaction tubes (10c).

5. Method according to claim 1, which is carried out in such a way that the maximum reaction temperature is not exceeded in at least 30% of each of the reaction zones (11, 12, 13) and the minimum reaction temperature is not undershot.

6. Method according to claim 5, which is carried out in such a way that in a second reaction zone (13), the maximum reaction temperature does not exceed a higher percentage and the minimum reaction temperature is not undershot to a greater extent than in a first reaction zone (11, 12).

7. Method according to claim 1, wherein the reactor (10) has at least three reaction zones and the gas mixture is passed through an initial reaction zone (11) it is passed through a first reaction zone (12) and a second reaction zone (13).

8. Method according to claim 7, wherein a catalyst bed (13a) of the second reaction zone (13) is formed with a higher catalyst loading and/or catalyst activity per space unit than a catalyst bed (11a) of the initial reaction zone (11) and the first reaction zone (12).

9. Method according to claim 1, wherein catalyst beds (11a, 12a, 13a) of the reaction zones (11, 12, 13) each have a proportion of active catalyst of at least 0.1% by weight.

10. Method according to claim 1, wherein the reaction zones (11, 12, 13) are temperature-controlled by means of one or more temperature control agent flows (105, 106).

11. Method according to claim 10, wherein a cooling system is provided with a plurality of temperature control agent flows (105, 106), wherein at least one of the plurality of temperature control agent flows (105, 106) is used for cooling only one or only one part of the reaction zones (11, 12, 13).

12. Method according to claim 1, wherein a process gas containing water is removed from the reactor (10) and wherein the method comprises adjusting a water partial pressure in the process gas removed from the reactor (10) to a value in a range between 0.5 and 5 bar (abs.).

13. System (100) for producing ethylene and acetic acid, which is designed to subject ethane to an oxidative dehydrogenation,
- wherein the system (100) for the oxidative dehydrogenation has a reactor (10) comprising a plurality of reaction zones (11, 12, 13),
- wherein means are provided that are designed to pass a gas mixture comprising ethane successively through the reaction zones (11, 12, 13),
- wherein at least two of the plurality of reaction zones (11, 12, 13) comprise catalysts of a same catalyst type and means are provided that are designed to subject the at least two reaction zones (11, 12, 13) to varying temperature influences,
- wherein the catalysts of the same catalyst type are catalysts comprising molybdenum, vanadium, and niobium in the same basic formulation which are provided in different concentrations or contents per unit space, and
- wherein the oxidative dehydrogenation is performed in a temperature range of 240 to 500° C. and a pressure range at an inlet of the reactor of 1 to 10 bar absolute pressure.

14. System (100) according to claim 13, comprising means designed to remove a process gas containing water from the reactor (10) and to set a water partial pressure in the process gas removed from the reactor (10) to a value in a range between 0.5 and 5 bar (abs), in particular between 0.7 and 3 bar (abs), depending on a predetermined product ratio of acetic acid to ethylene.

* * * * *

UNITED STATES PATENT AND TRADEMARK OFFICE
CERTIFICATE OF CORRECTION

PATENT NO. : 12,012,377 B2
APPLICATION NO. : 15/734497
DATED : June 18, 2024
INVENTOR(S) : Mathieu Zellhuber et al.

Page 1 of 1

It is certified that error appears in the above-identified patent and that said Letters Patent is hereby corrected as shown below:

On the Title Page

Item (30) should be added with the following data:
-- (30) Foreign Application Priority Data
Jun. 21, 2018 (EP) 18179086 --

Signed and Sealed this
Twenty-fifth Day of February, 2025

Coke Morgan Stewart
*Acting Director of the United States Patent and Trademark Office*